United States Patent [19]

Hirabayashi

[11] Patent Number: 5,099,536
[45] Date of Patent: Mar. 31, 1992

[54] ELECTRIC TOOTHBRUSH

[75] Inventor: Akira Hirabayashi, Matsumoto, Japan

[73] Assignee: Kabushiki Kaisha Izumi Seiki Seisakusho, Nagano, Japan

[21] Appl. No.: 476,493
[22] PCT Filed: Apr. 3, 1989
[86] PCT No.: PCT/JP89/00353
§ 371 Date: Jun. 12, 1990
§ 102(e) Date: Jun. 12, 1990
[87] PCT Pub. No.: WO90/09123
PCT Pub. Date: Aug. 23, 1990

[30] Foreign Application Priority Data

Feb. 17, 1989 [JP] Japan ................................. 1-39002

[51] Int. Cl.$^5$ ............................................ A46B 13/02
[52] U.S. Cl. .................................... 15/28; 15/DIG. 1;
433/125; 433/130
[58] Field of Search ....................... 15/28, 29, 22.1, 23,
15/24; 433/103, 108, 109, 114, 125, 130, 131

[56] References Cited

U.S. PATENT DOCUMENTS 2,140,307 12/1938 Belaschk et al. .................... 15/28
3,757,419 9/1973 Hopkins ................................ 15/28
3,939,599 2/1976 Henry et al. ........................ 15/28

FOREIGN PATENT DOCUMENTS 3341465 5/1985 Fed. Rep. of Germany .......... 15/28
452961 9/1936 United Kingdom .................... 15/28

Primary Examiner—Edward L. Roberts

[57] ABSTRACT

In an electric toothbrush of the present invention, a head case is detachable from a main case, so that brushes on the head case can be easily washed and kept clean. The orientation of the brushes with respect to the main case can be changed, so that every tooth can be brushed well. A driving force of a motor is transmitted by first and second shafts and gears, so that the force can be positively transmitted to the brush even though the transmitting route is bent. Vibration of the electric toothbrush is less than conventional toothbrushes which alternately rotate brushes because the brushes are rotated by the first and second shafts. Holes of lead-pieces for connecting terminals have inwardly extending claws, and the terminals can be connected only by insertion into the holes, so that assembling steps can be reduced. If the tips of the claws are sharpened, the terminals are held tightly.

8 Claims, 9 Drawing Sheets (A)

ELECTRIC TOOTHBRUSH

BACKGROUND OF THE INVENTION

1. Field of the Invention

The present invention relates to an electric toothbrush which provides improved brushing in gaps between teeth.

2. Description of The Related Art

Conventionally, several ways of brushing teeth have existed. One way of brushing is by manually brushing with a toothbrush (a so called hand brush), which has many hairs thereon. With this toothbrush, there are two major methods for effectively brushing teeth, one is a "Scraping Method" in which the toothbrush, whose tips of the hairs of the brush contact the user's teeth, is reciprocated. Another method is a "Bass Method" in which the toothbrush, whose tips of the hairs of the brush contact a bonder between the teeth and gums by inclining the head section of the toothbrush about 45 degrees, and vibratins the head back and forth.

Another known way of brushing teeth is with an electric toothbrush in which a hand brush is attached to a drive section having a motor therein so as to linearly reciprocate the brush.

When using the hand-held type of brush, despite the known effective methods for brushing teeth such as the Scraping Method, the Bass Method, etc., it is difficult to master these methods, and there is an individual difference in brushing technique so that all users cannot brush equally as well even when learning the same techniques. The number of people who cannot brush effectively far outnumber people who can brush well. It is especially difficult to remove food particles on teeth which are stuck in gaps between teeth, on borders between the teeth and gums and concave sections of teeth.

Electric toothbrush are also known which can change between the Scraping Method and the Bass Method (e.g. Japanese Provisional Patent Publication (Kokai) Gazette No. 61-103404). In this electric toothbrush, however, rotary movement of a motor is converted to reciprocating movement, so that a large vibration is transmitted to a drive section and user the feels uncomfortable. Further, the brushing direction of the toothbrush is fixed, so that there are some portions of the mouth which are difficult to brush.

DISCLOSURE OF THE INVENTION

One object of the present invention is to provide an electric toothbrush which can remove food particles stuck in gaps between the teeth and on borders between teeth and gums, and which can comfortably brushing directions, and whose head section is detachable from a main case for washing.

Another object of the present invention is to provide an electric toothbrush having a built-in storage battery, which can be easily connected to charge-terminals without soldering.

The objects of the present invention are provided in an electric toothbrush comprising a motor in a main case and brushes driven by the motor, wherein the improvement comprises an intermediate case attached to a front end of the main case, the intermediate case includes an obtuse angle at a midsection thereof with respect to the axis of the main case, a head case is detachably provided at a front end of the intermediate case, a plurality of rotors are rotatably provided on an axis perpendicular to the axis of the head case, a plurality of gears are provided on outer circumferential faces of the rotors, respectively said gears being adjacent to and engaged with each other, brushes are provided on the rotors which project outward from a side wall of the head case, a first shaft is connected to the motor and inserted into an inner space of the intermediate case, a second shaft is rotatably held by the head case, one end of the second shaft being inserted into the inner space of the intermediate case, the second shaft being connected to the motor via a transmission system, and a gear provided at a remaining end of the second shaft is directly or indirectly engaged with the gears of the rotors.

The head case and intermediate case may be detachably assembled to each other by a bayonet engage system. The intermediate case may be detachable from the main case so as to place the brushes at a first position in which the brushes are projected toward a side where the intermediate case forms an obtuse angle. or at a second position on an opposite side of the first position.

With this structure, the head case is selectively detachable from the intermediate case connected to the main case, and the head case can be washed after use.

An inner frame in which the motor, a battery, switching mechanism, and the like are assembled therein may be accommodated in the main case.

Further, each of the plurality of rotors may have an indented or recessed section on an outer face thereof and a brush base having brushes may be detachably fitted in the recessed section.

Further, the built-in battery may be a storage battery, and lead-pieces for charging the storage battery, which have holes for connecting terminals and claws inwardly projected in the holes, may be adopted, in this case the claws can securely and elastically hold terminals.

EMBODIMENTS

Preferred embodiments of the present invention will now be described in detail.

Figure 1:
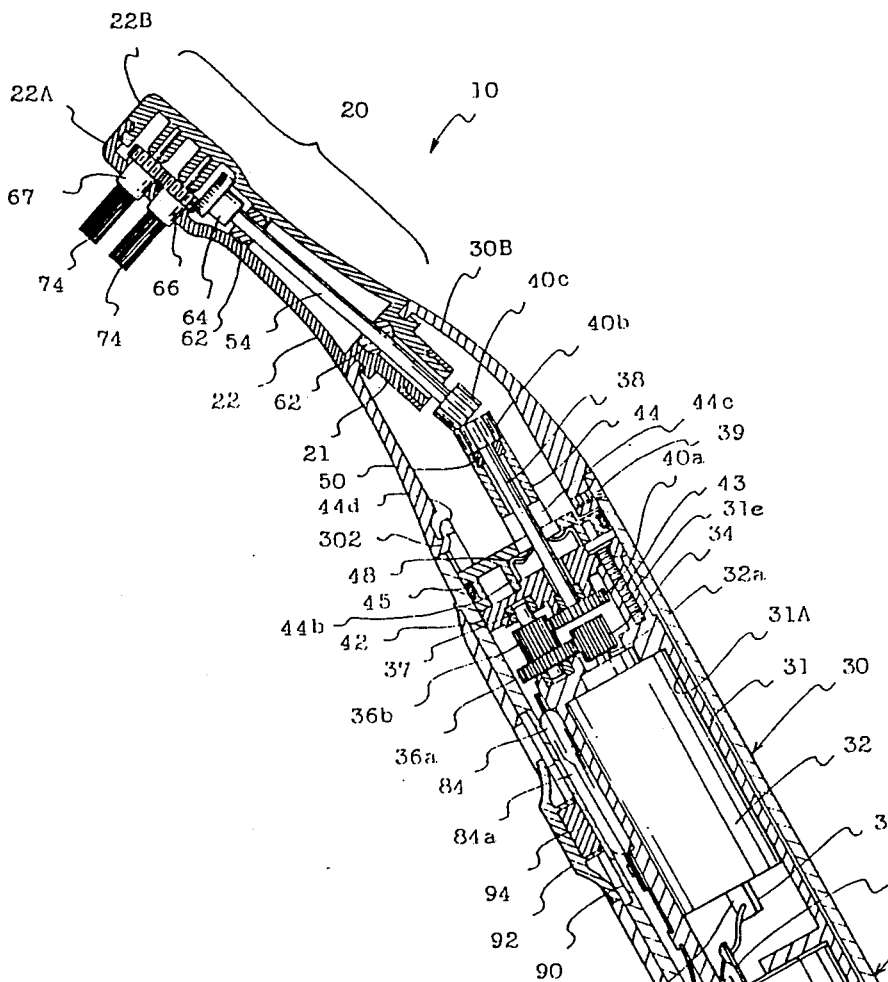
FIG. 1 shows a longitudinal sectional view of an electric toothbrush according to the present invention.
Figure 2:
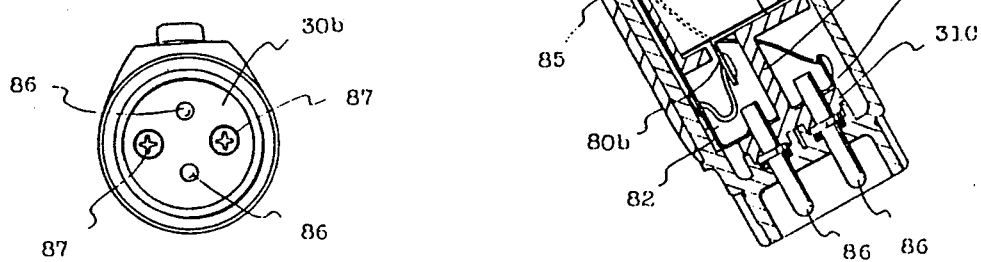
FIG. 2 shows a bottom view thereof.

FIG. 1 shows a longitudinal sectional view of an electric toothbrush of the present invention. FIG. 2 shows a bottom view thereof. The embodiment will be explained mainly with reference to FIG. 1.

Numeral 10 is an electric toothbrush. The toothbrush 10 has a head section 20 with brushes 74 at a front end thereof, and a drive section 30 having a drive mechanism for driving the brushes 74 of the head section 20 and also serving as a grip section.

The drive section 30 is covered with a main case 30A accommodating the drive mechanism which includes a motor 32 and a storage battery 80. An intermediate case 30B connects the main case 30A and the head section 20.

In the main case 30A, the motor, 32 storage battery 80 are assembled in a cylindrical inner frame 31. Two chambers 31A and 31B are arranged in a longitudinal direction within the inner frame 31 (See FIG. 3(A): The longitudinal sectional view of the inner frame). A motor 32 is provided in the forward chamber 31A. A drive shaft 32a of the motor 32 extends upward towards the intermediate case 30B and a gear 34 is fixed thereon.

The storage battery 80 is provided in the other chamber 31B. The storage battery 80 has terminals 80a and 80b extending from upper and lower ends thereof.

A lead-attachment 31C is provided at the lower end of the inner frame 31. The inner frame 31 is supported by a supporting member 31d which extends downward from the chamber 31B.

The lead-attachment 31C is divided into the front side and the rear side by the supporting member 31d, a lead-piece 82 is provided to the front side and a lead-piece 83 is provided to the rear side of the toothbrush, respectively. The lead-piece 82 is extended to the vicinity of the motor 32 along the outer face of the inner frame 31, and is connected to one terminal of a lead switch 84.

Within a glass case 84a of the lead switch 84, a pair of elastic switching pieces made of ferromagnetic material are provided facing each other. The switching pieces in the lead switch 84 contact each other when a magnet closes them.

Figure 3:
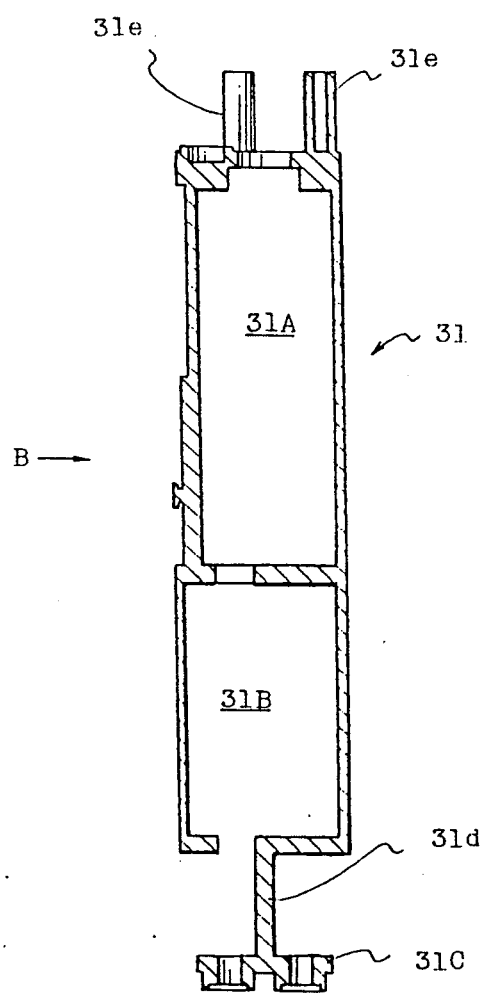
FIGS. 3(A), 3(B) show a sectional view and a plan view, respectively, in the direction of the arrow B of (A) of an inner frame.
Figure 3:
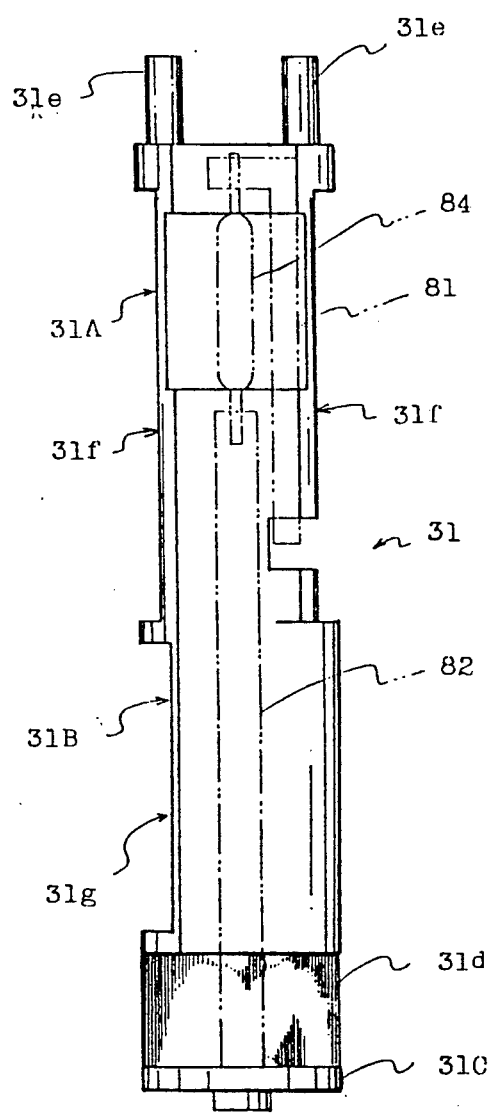

One of the switching pieces is connected to a terminal 32b of the motor 32 by a lead-piece 81 provided along the outer face of the inner frame 31 (See FIG. 3(B)). Another terminal 32c of the motor 32 is connected to the upper terminal 80a of the storage battery 80, and the terminal 80a is connected to the lead-piece 83 via a diode 85.

Note that, as shown in FIG. 3(B), the chamber 31A accommodating the motor 32 has openings 31f at both sides thereof and the chamber 31B has an opening 31g at one side thereof. The motor 32 and the storage battery 80 can be inserted into the chambers 31A and 31B through the openings 31f and 31g.

Figure 6:
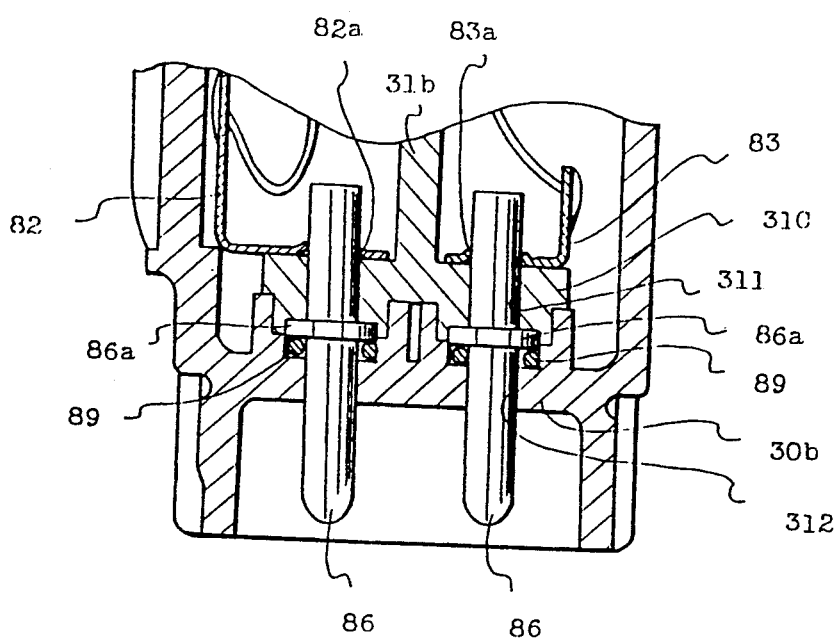
FIG. 6 shows a sectional view of a part of the electric toothbrush in which the terminals are attached.

FIG. 6 shows a sectional view of a part of the electric toothbrush which has terminals 86, 86 for charging the storage battery.

The lead-pieces 82 and 83 are respectively connected to terminals 86 for charging the storage battery. There are bored holes 311 within the lead-attachment 31c corresponding to the lead-pieces 82 and 83.

Figure 5:
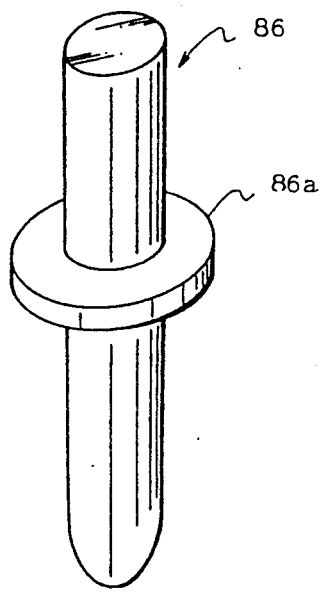
FIG. 5 shows a perspective view of a terminal for charging.
Figure 4:
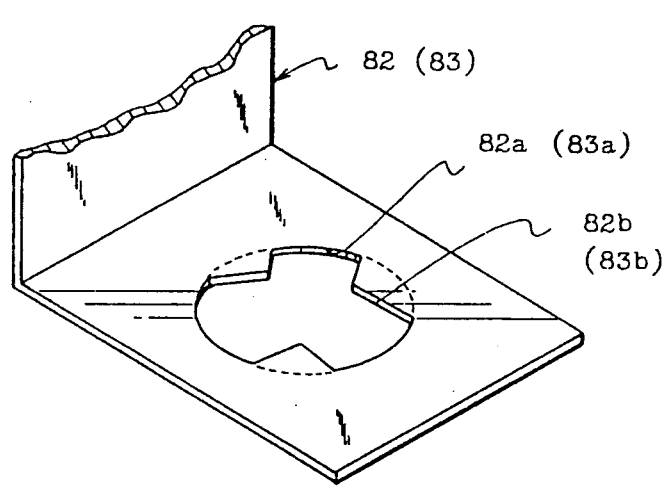
FIG. 4 shows a partial perspective view of a lead-piece.

There are bored holes 82a and 83a bored in the lead-pieces corresponding to the holes 311 in the lead attachment respectively. The diameter of the holes 82a and 83a are machine to fittingly receive an upper section of the terminals 86, and three inwardly receive an claws 82b and 83b are provided in each of the holes 82a and 83a (see FIG. 4). Each of terminals 86 has a flange section 86 at a midportion thereof (see FIG. 5).

When the terminals 86 are inserted into the holes 311, they are also respectively inserted into the holes 82a and 83a of the lead-pieces 82 and 83, so that the claws 82b and 83b elastically catch the head section of the terminals 86 and fix the terminals 86 therein. The flange sections 86a at the midportion of the terminals 86 contact a bottom face of the lead-attachment 31c, so that the terminals 86 are fixed tightly.

Note that the projected section on the bottom face of the lead-attachment 31c and the concave section formed on the bottom face 30b of the main case 30A can be fitted with each other. There are bored holes 312 through which the terminals 86 can be pierced from a bottom face 30b side of the main case 30A.

As described above, the drive mechanism including the motor 32, the storage battery 80, the lead switch 84, the and terminals 86 etc. is assembled in the inner frame 31.

With this structure, the drive mechanism can be easily attached in the main case 30A by inserting only the inner frame 31 accommodating the drive mechanism into the main case 30A. The inner frame 31 is fixed in the main case 30A by screwing a screw 87 into the lead-attachment 31c of the inner frame 31 from the bottom face 30b side of the main case 30A.

O rings 89 are provided under flange sections 86a to seal the terminals 86.

A concave section 90 on the outer face of the main surface 30A corresponds to the lead switch 84 and a switch 92 is slidably provided in the concave section 90. There is a magnet 94 fixed on the rear face of the switch 92. When the magnet 94 closes the switching pieces of the lead switch 84 in the main case 30A, the switching pieces contact each other and the motor 32 is driven.

The mechanism for transmitting drive force from the motor 32 to the brushes will be explained hereinbelow.

Three spacers 31e maintain a clearance between the inner frame 31 and a parting board 42. The parting board 42 and the inner frame 31 are fixed together by screwing a screw 43 into the spacers 31e from an upper face of the parting board 42.

The gear 34 of the drive shaft 32a of the motor 32 engages with a reduction gear 36a and a reduction gear 36b, provided on the same shaft 37 whereby reduction gear 36b, each of the reduction gears 36a and 36b being engages with a gear 40a which is provided at a lower end of a first shaft 38. The lower ends of the reduction gears 36a and 36b are pivotably supported on an upper face of the inner frame 31, and the upper end of the shaft 31 is also pivotably supported by the parting board 42.

The first shaft 38 pierces through the parting board 42 and projects upward. The first shaft 38 also pierces through a waterproof cap 44 and has a bevel gear 40b at the front end thereof.

Figure 7:
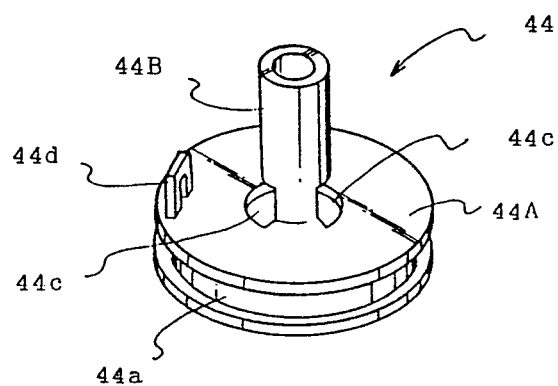
FIG. 7 shows a perspective view of a waterproof cap.

FIG. 7 shows a perspective view of the waterproof cap 44 which will be explained with reference to FIGS. 1 and 7.

The waterproof cap 44 has a board 44A contacting the parting board 42 and has a cylinder section 44B standing along the first shaft 38. There is a groove 44a on an outer circumferential face of the board 44A of the waterproof cap 44, and an O-ring 45 is provided in the groove 44a. A parting member 44b extends downward from the board 44A and rounds the first shaft 38. There is provided a sealing member 48 inside of the parting member 44b, and a center hole of the sealing member 48 tightly fits around the first shaft 38 to seal it. The lower end of the parting member 44b is fitted against a projection on the upper face of the parting board 42.

There is provided a bearing 50 at the front end of the cylinder section 44B of the waterproof cap 44 to support the first shaft 38. An opening 44c is provided in the border area (the base section) between the board 44A and the cylinder section 44B of the waterproof cap 44. The opening 44c is formed so as to introduce water, which has flowed along the first shaft 38 and has been sealed by the sealing member 48, toward the outside of the toothbrush.

One end section (the front side of the electric toothbrush 10) of the board 44A of the waterproof cap 44 is formed with an arch-like engaging section 44d.

The waterproof cap 44 prevents water from flowing into the main case 30A due to the O-ring 45 and the sealing member 48.

The intermediate case 30B is engaged with the upper end section of the main case 30A. The upper section of the intermediate case 30B is inclined slightly forward, and the first shaft 38 is extended to a midportion of the intermediate case 30B.

There is provided a hook 302, which is bent forward and can be engaged with an engaging section 44d of the waterproof cap 44 on the front face of the intermediate case 30B, and there is a screw hole bored at an opposing part of the intermediate case 30B from which the hook 302 is faced. With this structure, the intermediate case 30B can be assembled to the main case 30A by engaging the hook 302 of the intermediate case 30B with the engaging section 44d and by screwing a screw 39 into the upper end section of the main case 30A and the intermediate case 30B.

A second shaft 54 extends from the head section 20 and has a front end thereof inserted into the intermediate case 30B. There is a bevel gear 40c fixed at the front end of the second shaft 54. The bevel gear 40c is engaged with the bevel gear 40b of the first shaft 38. The second shaft 54 is supported by ball bearings 62 in a head case 22 of the head section 20.

Figure 8:
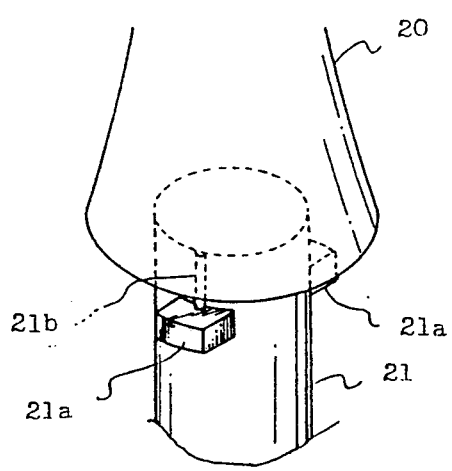
FIG. 8 shows a perspective view of a lower section of a head section.
Figure 9:
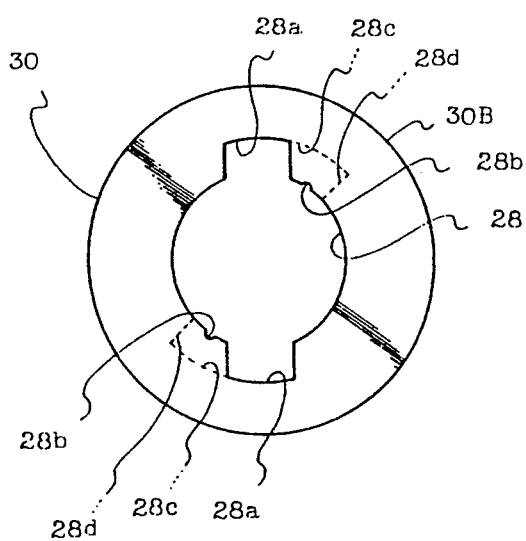
FIG. 9 shows a plan view of a front end of an intermediate case.

The interconnecting structure between the drive section 30 and the head section 20 will be explained with reference to FIGS. 8 and 9.

The lower end section of the head section 20 is a small-diameter neck section 21, and a pair of projections 21a are symmetrically formed on the outer face of the neck section 21. An inner-flange 28 extends inward at the front end of the intermediate case 30B, and a pair of guide grooves 28a are symmetrically grooved in the inner-flange 28. The head section 20 can be assembled by fitting the projections 21a in the guide grooves 28a of the inner flange 28 and by rotating the head section 20 to engage the head section with the intermediate case 30B. This structure of assembling the head section 20 to the intermediate case 30B is a so-called bayonet engage system.

There are engaging grooves 28c (shown by broken lines in FIG. 9), which allow the projections 21a to rotate in one direction in the inner-flange 28. The rotation of the projections 21a in the engaging grooves 28c is limited by walls 28d as stoppers. There are projecting sections 21b formed on the face of the neck section 21 between the projections 21a and the stepped area formed between the head section 20 and the neck section 21. Concave sections 28b, which can be engaged with the projections 21a of the neck section 21, are formed on the inner circumferential face of the inner-flange 28 of the intermediate case 30B. Assembling the head section 20 to the intermediate case 30B occurs by the bayonet engagement system, the projections 21b of the neck section 21 and the concave sections 28b of the inner-flange 28 holding their assembling status by the engagement.

The relationship of the engagement between the head section 20 and the intermediate case 30B can be reversed. Namely, grooves are formed on the circumferential face of the lower end section of the head section 20, projections are directed inwardly at the opening section of the upper end of the intermediate case 30B, and guide grooves, which correspond to the projections of the intermediate case 30B are formed so that the head section 20 can be fixed to the intermediate case 30B by fitting the guide grooves of the head section 20 to the projections of the intermediate case 30B.

Figure 10:
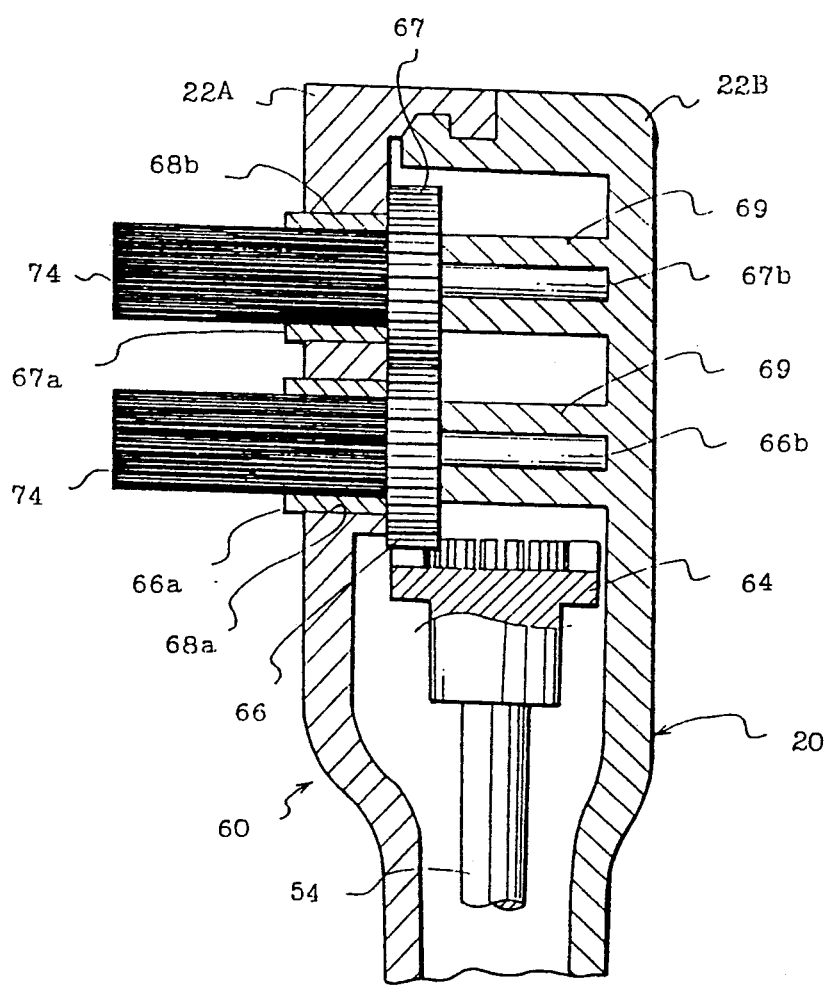
FIG. 10 shows an enlarged longitudinal sectional view of a brush section of the electric toothbrush.

The structure of the head section 20 will be explained hereinbelow with reference to FIGS. 1 and 10.

The head case 22 is formed by fitting a front head case 22A and a rear head case 22B together.

The front end of the head section 20 is a brush section 60 in which a line of brushes (a plurality of bunches of brushes) are rotatable. There is provided a ball bearing 62 in the base of the brush section 60. The second shaft 54 is supported by another ball bearing 62, which is provided at the lower section of the head case 22. A face gear 64 is fixed at the front end of the second shaft 54, which leads to an inner space of the brush section 60 of the head case 22. There are serially arranged rotors 66 and 67, which have gears engaging with the face gear 64 on their circumferential faces, in the brush section 60. Two circular holes 68a and 68b are bored on the front face of the front head case 22A of the brush section 60, and cylinder sections 66a and 67a, which are integrally formed on the front face of the rotors 66 and 67, project therefrom. Brushes 74 are fixed in the cylinder sections 66a and 67a.

Shafts 66b and 67b project from the rear face of the rotors 66 and 67, and the shafts 66b and 67b are inserted into bearings 69 projecting from the inner face of the rear head case 22B of the brush section 60.

Therefore, the driving force of the second shaft 54 rotates the rotor 66 via the face gear 64, and the force rotating the rotor 66 is transmitted to the rotor 67. With this structure, a rotors 66 and 67 rotate in the counter direction with respect to each other, so that the brushes 74 can easily hold their position in the mouth when brushes 74 contact teeth because the inertia of the two brushes 74 has been eliminated.

Figure 11:
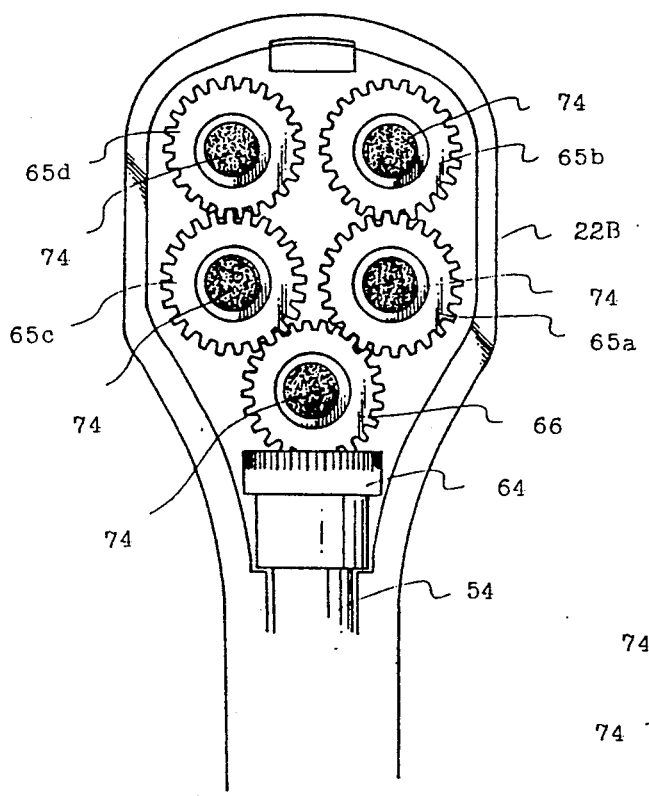
FIG. 11 shows a plan view of the brush section without a front brush case for showing an arrangement of brushes.
Figure 12:
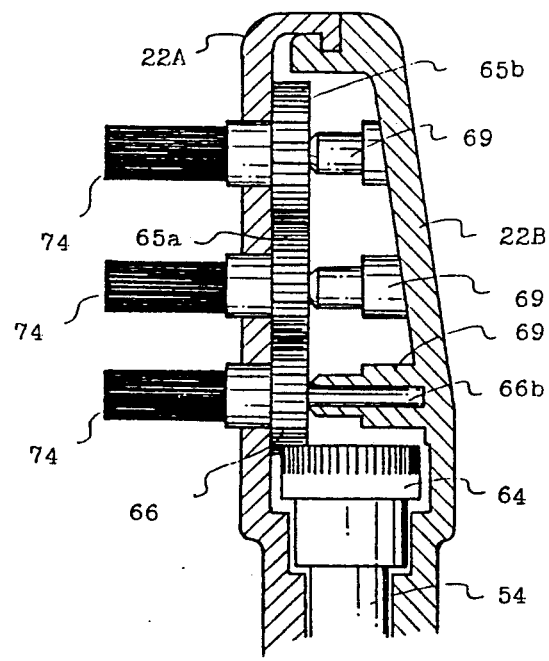
FIG. 12 shows a longitudinal sectional view of the brush section.

FIGS. 11 and 12 show another arrangement of brushes. FIG. 11 shows a plan view of the brush section 60 without the front case and FIG. 12 shows a longitudinal sectional view of the brush section.

In this example, the rotor 66 engages with the face gear 64 fixed at the front end of the second shaft 54, and a first group of serial rotors 65a and 65b, which engage with the rotor 66, and a second group of serial rotors 65c and 65d, which also engage with the rotor 66, are arranged in parallel. The structure of the rotors 65a–65d is the same as the rotors 66 and 67, so they have gears on their circumferential faces. This electric toothbrush has five rotors and each of the rotors has a brush 74. Shafts porojected from the rear face of the rotors 66 and 65a–65d are fitted in the bearings 69 projecting from the inner face of the rear head case 22B.

How to use the electric toothbrush having above described structures will be explained below.

First, terminals 86 are connected to an A.C. outlet to charge the storage battery 80.

When using the electric toothbrush, the brushes 74 are contacted with the user's teeth, and the switch 92 is turned to an on position, so that the switching pieces of the lead switch 84 contact each other thereby starting the motor 32.

The driving force of the motor 32 is transmitted to the first shaft 38 via the gear 34 fixed at the front end of the drive shaft 32a of the motor 32 and the reduction gears 36a and 36b.

The driving force is further transmitted to the face gear 64 to rotate rotors 66 and 67 and brush 74 via the bevel gear 40b fixed at the front end of the first shaft 38, the bevel gear 40c being fixed at the second shaft 54.

Upon sliding back of the switch 94, the motor 32 stops and the toothbrush is turned off.

After use, the head section 20 is rotated to detach from the drive section 30, and can be washed.

Figure 13:
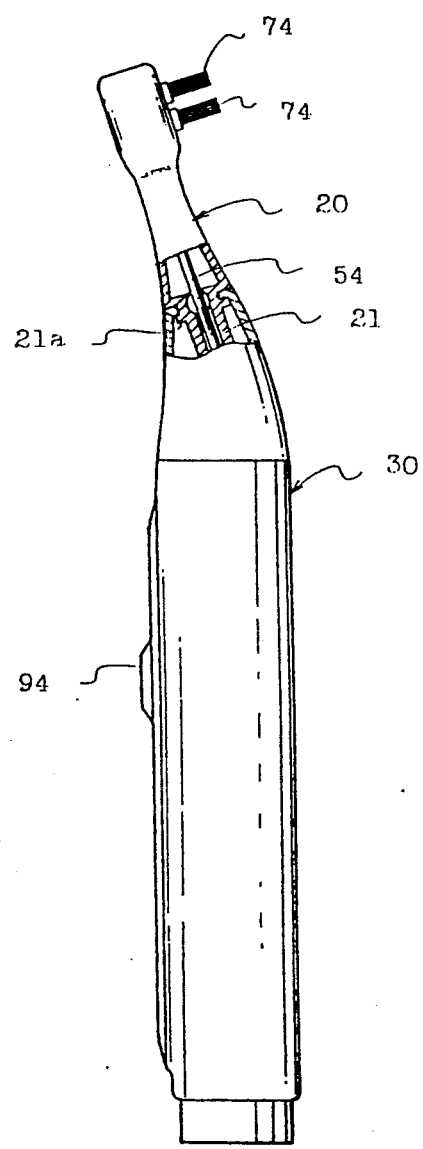
FIG. 13 shows a partial sectional view of the electric toothbrush whose head section is attached so as to face in an opposite direction of the brushes shown in FIG. 1.

Note in the electric toothbrush of FIG. 1, that the head section 20 and the intermediate case 30B are assembled to enable the brushes 74 to face forward of the main case 30A. However, as described above, the head section 20 can be attached to and detached from the intermediate case 30B by the bayonet engage system, and the projections 21a and the guide grooves 28a are respectively symmetrically arranged, so that the head section 20 can be invertedly attached to the intermediate case 30B. With this structure, as shown in FIG. 13, the brushes 74 can be attached to face toward the rear of the main case 30A. Facing the brushes 74 forward and backward, user can brush everywhere around his teeth with the electric toothbrush 10.

Figure 14:
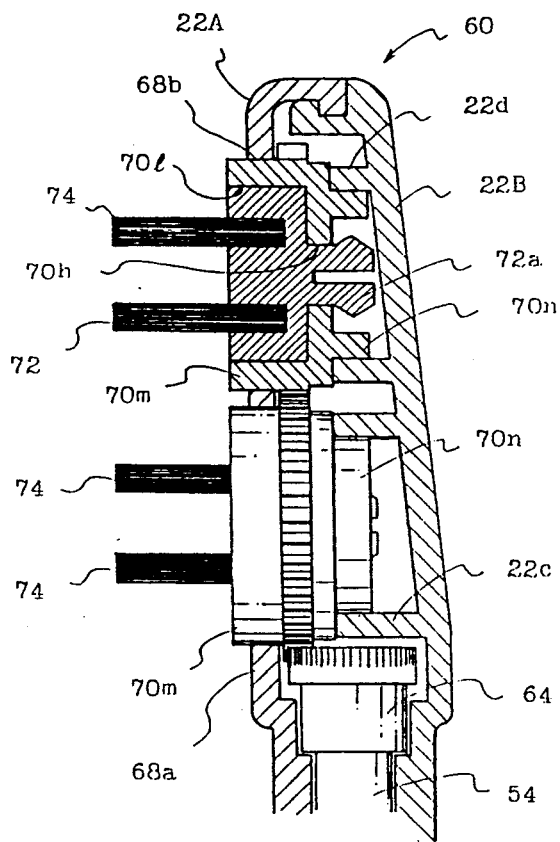
FIG. 14 shows a longitudinal sectional view of the brush section of another embodiment.
Figure 15:
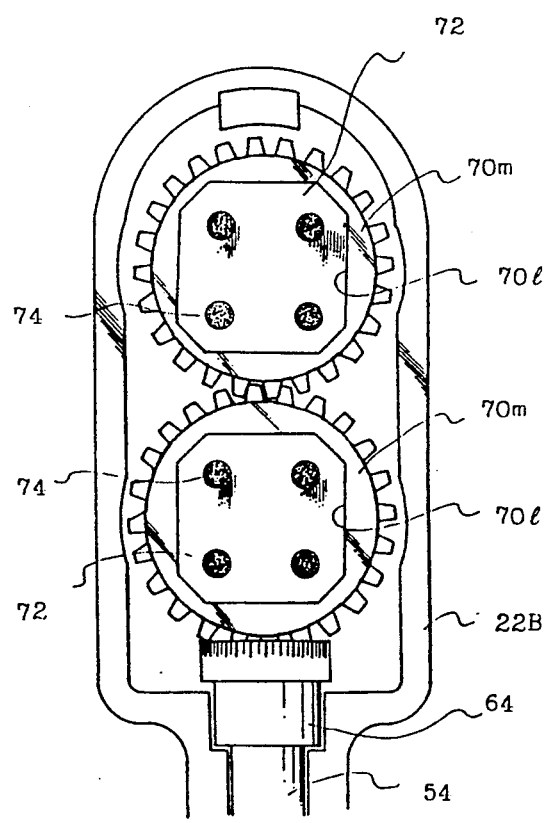
FIG. 15 shows a plan view of the brush section without the front head case.

Another embodiment will be explained with reference to FIG. 14. Note that FIG. 15 shows a plan view of the brush section of this example without the front head case.

There are two circular holes 68a and 68b bored in the front head case 22A of the brush section 60 and upper ends of brush cases 70 are projected therefrom.

The diameter of the brush cases 70 is slightly smaller than the holes 68a and 68b, and the brush cases 70 have cylindrical engaging sections 70m, which project outward from the inner space of the brush section 60, and engage cylinders 70n, which extend backward from the rear face of the engaging sections 70m. The cylinders 70n are engaged with guide cylinders 22c and 22d, which correspond to the holes 68a and 68b and which project from the inner face of the rear head case 22B of the brush section 60.

Gears are provided on the outer circumferential faces of the engaging sections 70m, the outer diameter of the gears being larger than the holes 68a and 68b. Therefore, the brush cases 70 cannot be removed from the holes 68a and 68b. The face gear 64 rotatably engages with and rotates to the brush cases 70.

Rectangle recessed sections 70l are formed in the engaging sections 70m, and through-holes 70h are bored at the center of the recessed sections 70l. Split claws 72a are provided on the bottom faces of approximately rectangular brush bases 72, which can be fitted into the recessed sections 70l of the brush cases 70. Upon fitting of the brush bases 72 into the recessed sections 70l of the brush cases 70, the split claws 72a fit into the through-holes 70h to fix the brush cases 70 within the recessed sections 70l. The brush bases 72 are changable.

Brushes 74 are fixed on the upper faces of the brush bases 72.

Each of the plurality of rotors has a brush case 70, which has a gear on the outer circumferential face, and the brush base 72 includes brushes 74 fixed thereon.

In this embodiment, four brushes 74 are fixed on the brush bases 72. However, the number is not limited, and the number of brushes 74 fixed on one brush base 72 may be one, three, five, six or more.

In above described embodiments, the motor 32 is driven by the storage battery 80 but it may be driven by a dry battery. Further, it may be directly connected to the A.C. outlet. Furthermore, gears for transmitting driving force may be made of plastic for anticorresiveness.

Preferred embodiments of the present invention have been described but the present invention is not limited to these embodiments. For example, the arrangement of brushes can be the user's option, so modifications can be allowed without deviating the scope of claims.

EFFECTIVENESS OF THE INVENTION

The present invention has the above described structures and following advantages:

It is easy to wash the toothbrush and to keep it clean because the head case can be detached from the main case of the electric toothbrush. It is able to effectively brush every tooth because the direction of the brushes with respect to the main case can be changable. It is easy to brush sides of the teeth because the head section is inclined forward with respect to the main case. A driving force of the motor can be certainly transmitted because the first and second shafts and gears are combined to angle a transmission route of the force.

Vibration of the electric toothbrush is less than conventional ones which alternately rotate brushes in both directions because each brush rotates in one direction. The position of brushes can be stabilized in the mouth because each pair of adjacent brushes rotate in opposite directions and the inertia is removed.

Assembling steps of the toothbrush can be reduced because there are provided claws projecting into inward the holes of the lead-pieces connecting the terminals for charging the storage battery and the terminals can be connected by only inserting the claws into the holes. If the tips of the claws are formed sharp, the holding force of the claws working against the terminals can be increased.

INDUSTRIAL APPLICABILITY

With the electric toothbrush of the present invention, the brushes can remove sordes between teeth and brush teeth up cleanly.

I claim:

1. An electric toothbrush, comprising:
   a main case serving as a grip section;
   an intermediate case attached to a front end of said main case, said intermediate case being angled at a midportion thereof to form an obtuse angle with respect to a longitudinal axis of said main case;
   a head case detachably provided to a front end of said intermediate case;
   a plurality of gears housed within said head case, said plurality of gears being rotatable on an axis perpendicular to a longitudinal axis of said head case, adjacent ones of said plurality of gears being engaged with each other;

at least one brush provided on each of said plurality of gears and, said at least one brush projecting outward from a side wall of said head case;

a motor housed within said main case;

a first shaft connected to said motor and inserted into an interior of said intermediate case;

a second shaft rotatably held by said head case, one end of said second shaft being inserted into the interior of said intermediate case and a remaining end of said second shaft being selectively engaged with at least one of said plurality of gears housed with said head case; and means for transmitting power from said motor to said first and second shafts thereby imparting rotation to said plurality of gears housed within said head case.

2. The electric toothbrush according to claim 1, wherein said head case and intermediate case are releasably engaged with each other by a bayonet connection.

3. The electric toothbrush according to claim 2, further comprising means for preventing other than a predetermined rotation of said head case with respect to said intermediate case, said means for preventing being provided at an engagement section between said head case and said intermediate case so as to selectively place said brushes at a first position in which said brushes are projected toward a first side of said intermediate case and at a second position opposite to said first position.

4. The electric toothbrush according to claims 1, 2 or 3, further comprising an inner frame in which said motor, a battery, and a switching mechanism are accommodated within said main case, said inner frame being fixed within said main case.

5. The electric toothbrush according to claim 4, wherein said battery is a storage battery, and further comprising means for charging said storage battery, said means for charging including leads extending from said storage battery and terminals connected to said leads, said leads including apertures having claws formed at an inner periphery thereof for securely gripping ends of said terminals therein.

6. The electric toothbrush according to claim 5, wherein tips of said claws are sharpened to increase a gripping strength thereof with respect to said terminals.

7. The electric toothbrush according to claim 5, further comprising an attachment to which said leads are connected, said attachment having through-holes corresponding to the apertures of said leads and wherein each of said terminals connected to said leads includes a flange section at a midportion thereof, said terminals being inserted into said through-holes and said apertures, said terminals being elastically held by said claws, and the flange sections of said terminals contact a rear face of said attachment.

8. The electric toothbrush according to claims 1, 2 or 3, wherein said plurality of gears have a recessed area formed on an outer planar face thereof and further comprising a brush base detachably fitted within said recessed area, said brush base having at least one brush mounted thereon.

* * * * *